(12) United States Patent
Schneider

(10) Patent No.: US 7,294,144 B1
(45) Date of Patent: Nov. 13, 2007

(54) PRESERVED IMPLANTABLE VESSEL DERIVED FROM A HUMAN UMBILICAL CORD OR PLACENTA

(76) Inventor: James R. Schneider, 5990 Stoneridge Dr., Suite 118, Pleasanton, CA (US) 94588

( * ) Notice: Subject to any disclaimer, the term of this patent is extended or adjusted under 35 U.S.C. 154(b) by 0 days.

(21) Appl. No.: 09/307,956

(22) Filed: May 10, 1999

Related U.S. Application Data

(63) Continuation-in-part of application No. 09/132,021, filed on Aug. 10, 1998, now abandoned.

(51) Int. Cl.
- *A61F 2/00* (2006.01)
- *A61F 2/04* (2006.01)
- *A61L 17/00* (2006.01)
- *A61K 2/02* (2006.01)

(52) U.S. Cl. .............. 623/1.1; 623/23.64; 600/36; 424/423; 8/94.11

(58) Field of Classification Search .............. 623/1.11, 623/1.13, 1.14, 1.35, 1.1, 11.11, 23.65, 23.72; 600/36; 435/1.1, 1.2; 424/422–424; 8/94.11
See application file for complete search history.

(56) References Cited

U.S. PATENT DOCUMENTS

| | | | |
|---|---|---|---|
| 3,894,530 A | * | 7/1975 | Dardik et al. ............ 600/36 |
| 3,974,526 A | | 8/1976 | Dardik et al. |
| 3,988,782 A | | 11/1976 | Dardik et al. |
| 4,239,492 A | | 12/1980 | Holman et al. |
| 4,801,299 A | | 1/1989 | Brendel et al. |
| 5,131,908 A | | 7/1992 | Dardik et al. |
| 5,800,540 A | * | 9/1998 | Chin .................. 623/1.12 |
| 5,876,432 A | * | 3/1999 | Lau et al. ............ 623/1.13 |
| 6,090,136 A | * | 7/2000 | McDonald et al. ...... 623/1.23 |

OTHER PUBLICATIONS

Rat Epigastric Pedicle Model: A Clinically Relevant Evaluation of 1-MM PTFE Grafts; Barttelbort et al; 1985; 233-236.

Microsurgical Application of Freeze-Dried Venous Allografts; Pratt et al; 1985; 211-218.

Microsurgical Application of Freeze-Dried Arterial Allografts; Pratt et al; 625-629.

Experimental Freeze-Dried Microarterial Allografts in Rabbits; Pratt et al; 1987; 1-15.

\* cited by examiner

*Primary Examiner*—David J. Isabella
(74) *Attorney, Agent, or Firm*—Carol L. Francis; Bozicevic, Field & Francis LLP

(57) ABSTRACT

A preserved vessel isolated from a human umbilical cord or placenta and lyophilized for use as an allograft which improves blood supply to human tissue without antigenicity.

40 Claims, 1 Drawing Sheet

PRESERVED IMPLANTABLE VESSEL DERIVED FROM A HUMAN UMBILICAL CORD OR PLACENTA

CROSS-REFERENCE TO RELATED APPLICATIONS

The present application is a Continuation-in-Part of U.S. patent application Ser. No. 09/132,021; filed 10 Aug. 1998 now abandoned.

BACKGROUND OF THE INVENTION

The present invention relates to a novel vascular allograft.

Since about the year 1900, much research effort has been undertaken to provide substitute vascular conduits in surgical situations. In essence, a substitute or artificial vein for the natural vein in a mammalian species provides oxygen to blood tissues and removes venous blood from the tissues in the same manner. Many situations have been identified where substitute vessels are needed:

1. Replacement vessels are needed for supplying ischemic tissue, which cannot obtain enough oxygen and nutrients to stay alive. Such a vessel may be required in cases of injury to a blood vessel which cannot be primarily repaired, or when a vessel is excised as a result of tumor mass or other obstructions.

2. A bypass vessel may be employed to circumvent an obstruction and may be emplaced by an end-to-side connection. Thus, blood is permitted to flow around the obstruction through this expedient.

3. Collateral vessels may be employed to provide circulation to ischemic tissue without disrupting inefficient vessels.

4. A shunt may be devised, such as one needed for renal dialysis. For example, a vessel may be placed in the forearm of a human in a subcutaneous position to permit venepuncture allowing dialysis to proceed.

5. A vessel extender may be provided in cases of free tissue transfer. In other words, such extenders may be employed where the existing pedicle of the composite graft is not sufficiently long.

In general, the mammalian circulation system operates when the heart pumps blood carrying oxygen and nutrients through arteries to all of the tissues of the body. Subsequently, oxygen-deprived blood and metabolic byproducts are returned by the veins to replenish oxygen for passing such metabolic byproducts to waste. The veins have lower blood pressure than the arteries. Thus, the blood returns to the heart by back pressure from the arterial system, muscular action in the limbs, and gravity in the case where portions of the body lie above the heart. Low venus blood from the lower limbs is facilitated by one-way valves in the walls of the veins. For example, the saphenous veins permit flow toward the heart but prevent backflow therefrom. Thus, veins in this aspect constitute a one-way flow system.

In the past, it has been found that autogenous grafting has achieved success without evidence of graft rejection. In allografts, however, tissue removed from one person and implanted in another person typically has resulted in graft rejection, requiring the use of immunosuppressive drugs. It should be noted that the use of heterografts (xenografts) has been uniformly unsuccessful due to rapid rate of graft rejection. Within the last 50 years, tissue banks supplying frozen tissue have been established. Such banks, however, have not completely solved the problem of antigenic rejection with respect to allograft tissue.

Modified vascular conduits have been provided utilizing chemical preservatives such as glutaraldehyde in conjunction with a mesh frame work. Reference is made to U.S. Pat. Nos. 3,988,782 and 3,974,526 in which a process for producing tubular prostheses is described. Unfortunately, such preservation system is relatively short-lived.

Artificial grafts, such as ones constructed of polytetrafluoroethylene (PTFE) have proved successful when used with larger diameter vessels, but unsuccessful in smaller diameter vessels. Further, anastomosis between the PTFE graft and different sized vessels is difficult. In addition, the PTFE grafts are rigid and don't propagate the pulse within the body. Moreover, PTFE grafts tend to kink if bent beyond a certain degree.

Autologous grafts are commonly used in heart bypass surgery. That is to say, saphenous veins from human legs have been harvested and transplanted into the heart as a bypass vessel. In addition, such autologous grafts have also been used as a dialysis shunt, for free tissue transfers, and as an added vascular pedicle. Although successful in many aspects, saphenous veins are usually thin walled and hard to handle. During harvesting procedures, saphenous vessels possess tributaries which must be tied off causing flow turbulence in the patients circulation system. Also, saphenous veins have varying widths and may include one-way valves which must be eliminated. In addition, extra operating time is required for harvesting vessels from a patient's leg prior to implantation. After harvesting, lower limb complications may occur in the patient such as delayed healing or painful scars in the leg. Moreover, arteries are not usually available for use as an autograft. Arteries harvested from a cadaver for use as an allograft have exhibited graft rejection problems. However, arteries if usable, are easier to handle because they are thicker walled, contain no one-way valves, and possess less tributaries to be tied off or isolated. It has been found historically that arteries, specifically the media layer, will spasm if used as a graft leading to occlusion of the vessel.

Lyophilization of human and other mammalian tissue has been employed to preserve bone, fascia, tendons, cartilage, ligaments, and the like. U.S. Pat. Nos. 5,656,498 and 5,690, 963 described freeze-drying of blood cells and the like for reuse. Several publications entitled *Rat Epigastric Pedicle Model: A Clinically Relevant Evaluation Of 1-mm PTFE Grafts*, Barttelbort et al; *Microsurgical Application Of Freeze-Dried Venous Allografts*, Pratt et al; *Microsurgical Application Of Freeze-Dried Arterial Allografts*, Pratt et al; and *Experimental Freeze-Dried Microarterial Allografts In Rabbits*, Pratt et al indicate that lyophilization may reduce or eliminate graft rejection in femoral arteries in rats and rabbits.

U.S. Pat. No. 4,239,492 described a method of preparing vascular grafts from umbilical cords using chemical preservatives.

U.S. Pat. No. 4,801,299 describes the processing of umbilical cords which are treated with using a detergent and are lyophilized just prior to implantation.

U.S. Pat. No. 5,131,908 in which a mandrel is employed to control the size and shape of a vessel to be preserved. Multiple chemical entities are applied to the vessel for cleaning and denaturing without lyophilization in the processing stage. The preservation technique described in this patent is primarily designed to denature the vessel in order to remove all cellular components, leaving an extra cellular matrix for implantation.

The provision of a preserved vessel isolated from the human umbilical cord for use as an allograft would be a notable advance in the medical field.

BRIEF SUMMARY OF THE INVENTION

In accordance with the present invention a novel and useful preserved vessel from a human umbilical cord is herein provided for the purpose of implantation as an allograft.

Human umbilical cords having two arteries and one vein, or the human placenta with multiple smaller arteries and veins are used as the source for the vessels of the present invention. The vessels are isolated from the umbilical cord by blunt and sharp dissection techniques. With continuing irrigation during this process, the vessels are separated from each other and the sheath of the umbilical cord. Stents, typically one millimeter or larger composed of plastic, nylon, and the like are placed within the lumen of the vessels to facilitate vessel handling, and to prevent the contact of opposite vessel walls during subsequent processing and storage, described hereinafter.

Each vessel and stent is placed in a moist cotton carrier and positioned within a freeze-drying canister. The canister may be refrigerated until the freeze-drying process takes place. A vacuum is applied to the canister when placed in a standard freeze-dryer for a requisite period of time and at an acceptable temperature, known in the art. It is believed that the water within the vessels being lyophilized passed from a frozen crystalline state into the vapor state by the process of sublimation. This process avoids disruption of the integrity of the cellular structure of the vessels which normally occurs during passing of liquid water into a solid state. Following freeze-drying each vessel specimen may be stored in the canister at room temperature in its lyophilized condition and with the vacuum seal being maintained.

Rehydration of the vessels takes place by simply removing the vessels with the enclosed stents and the cotton carrier from the freeze-drying canister, and soaking the same in heparinized saline for 20 minutes. After discarding of the cotton carrier, the plastic stent is maintained within the vessel until the vessel is trim and implanted by standard vascular anastomosis techniques.

While in the foregoing it may be apparent that a novel and useful preserved vessel useful for implantation is herein provided.

It is therefore an object of the present invention to provide a preserved vessel for implantation which derives from a human umbilical cord or placenta.

Another object of the present invention is to provide a preserved vessel derived from a human umbilical cord which may be implanted as an allograft without rejection by a human entity.

Another object of the present invention is to provide a preserved vessel derived from a human umbilical cord or placenta for implantation which possesses a relatively long shelf life.

A further object of the present invention is to provide a preserved vessel derived from a human umbilical cord or placenta which may be rehydrated for use following a lyophilization process.

Yet another object of the present invention is to provide a preserved vessel derived from a human umbilical cord or placenta which, when implanted, provides a supply of blood and nutrients to human tissue.

Another object of the present invention is to provide a preserve vessel derived from a human umbilical cord or placenta which may be implanted safely, obviating harvesting of veins from a patient during certain surgical procedures.

Another object of the present invention is to provide a preserved vessel derived from a human umbilical cord possessing uniform width, and lacking tributaries and valves.

A further object of the present invention is to provide a plentiful supply of preserved vessels derived from a human umbilical cord for implantation.

Another object of the present invention is to provide a preserved vessel for eventual implantation, which possesses straight and branded vessels without valves.

The invention possesses other objects and advantages especially as concerns particular characteristics and features thereof which will become apparent as the specification continues.

For a better understanding of the invention references made to the following detailed description of the preferred embodiments which should be referenced to the prior described drawings.

DETAILED DESCRIPTION OF THE PREFERRED EMBODIMENTS OF THE INVENTION

Various aspects of the present invention will evolve from the following detailed description of the preferred embodiments thereof which should be referenced to the prior described drawings.

The preserved vessel of the present invention 10 is obtained from a human placenta having an attached umbilical cord following child birth. It has been found that umbilical cords serve as an advantageous source of vessels for ultimate implantation since umbilical cord vessels lack branching, are generally of uniform cylindrical width, and contain no one-way valves, as do saphenous veins. The human umbilical cord contains two arteries and one vein, each of which are suitable for implantation. The placenta and umbilical cord unit is refrigerated, but not frozen or placed in a preservative, for recovery of the vessels within a six hour period. Cooling is maintained during transportation to the harvesting site.

The donor unit is received at a processing center, where three separate and sequential processing stations are prepared, each using sterile environment, instruments, and technique. At the first station the umbilical cord and placenta are grossly rinsed, blot dried briefly with absorbent towels, and then placed at the second station with the umbilical cord elongated.

At the second station the umbilical cord and placenta are inspected to insure that the cord contains two arteries and one vein. Any two-vessel umbilical cords are not utilized in the present invention. The point of dividing the umbilical cord from the placenta will vary according to length and size needs. In general, however the umbilical cord will be transversely incised at a point 1.0-cm from entry into the placenta. The placenta is passed to the third station. The processing of the umbilical cord at the second station involves identifying the ends of the arteries and veins and thoroughly irrigating each vessel using smooth cannulation, with a heparin solution (300 U/ml). This process physically removes fetal blood within the vessels and chemically inhibits clot formation from remaining platelets. The umbilical cord sheath is then incised longitudinally. Using blunt and sharp dissection techniques, the vessels are separated from the sheath and from the interposed Wharton's jelly. The arteries are easily identified from the helical arrangement around the thicker wall umbilical vein. The three vessels are then bluntly detached from one another such that the arteries maintain a serpentine configuration. The vessels are then incised transversely to provide varying vessel lengths as required.

Figure 1:
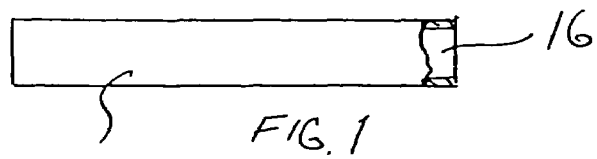
FIG. 1 is a side elevation view of a raw vascular segment from a human umbilical cord.
Figure 2:
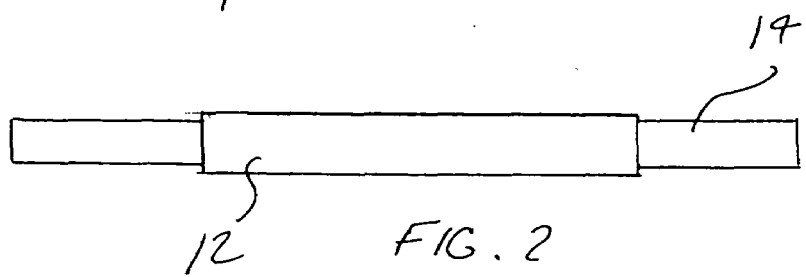
FIG. 2 is a side elevational view depicting the raw umbilical cord vascular segment having a stent placed within its lumen.
Figure 3:
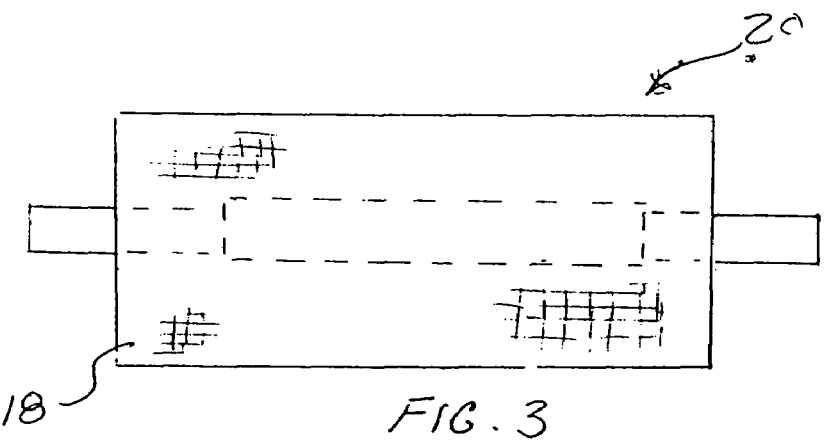
FIG. 3 is a top plan view of the combined vascular segment and stent within a gauze carrier.
Figure 4:
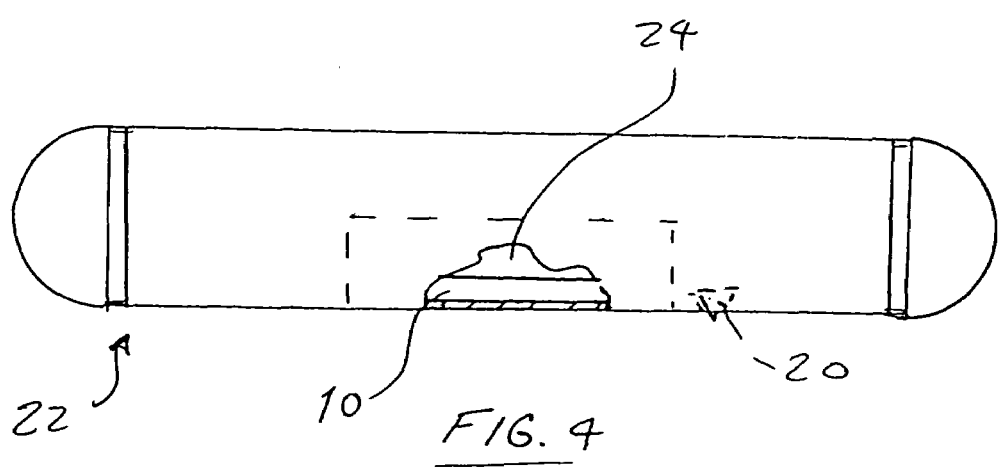
FIG. 4 is a side elevational view of a freeze-drying canister containing the lyophilized vascular segment, stent, and gauze carrier depicted in FIG. 3.

FIG. 1 represents a vascular segment 12 at this point in the recovery process. Vessel 12 is then fitted with a nylon stent 14 which passes through the lumen or passageway 16 of vessel segment 12, FIG. 2. Vessel 12 and stent 14 are then placed in a moist gauze carrier 18, FIG. 3. At this point, the vessels within the umbilical cord, such as vessel 12, have been protected from freezing, contamination, rough handling, and desiccation. The unit 20, FIG. 3, consisting of the vessel segment 12, stent 14, and gauze carrier 18, is then positioned or placed within a canister 22, depicted schematically in FIG. 4. Canister 22 is sealable and capable of holding a vacuum. Needless to say, canister 22 is sterilized. Canister 22 may be refrigerated temporarily pending transfer to a commercial freeze drier. Each canister, such as canister 22, is marked to identify tissue origin and to record the length, size, and branching, if any. Canister 22 is then placed in a freeze drier, such as a Virtis freeze drier, and freeze-dried. Typically this process takes place between minus 35 degrees centigrade and minus 60 degrees centigrade under a vacuum of, typically, 0.4 atmospheres, and over a 24 hour period. Such freeze-drying process allows removal of 90% of the water in vessel segment 12 through the process of sublimation of the same. Thus, damage to the structural integrity of vessel segment 12 is avoided and, it is theorized that, freeze-drying process destroys the antigen responsible for ultimate rejection of the graft in a human. When the canister 22 and unit 20 containing the lyophilized vessel segment 10 may be stored for a relatively long period of time, measured in years. During such storage, which may be at room temperature, the canister 20 is left intact, including the maintaining of a vacuum within chamber 24 of canister 22.

A third station would receive the placenta with its umbilical stump. At this station, the remaining portions of the placenta and umbilical cord sheath stump are used to obtain arteries and veins contained therein, by dissection and processing techniques previously described in this application. The vessels in the placenta and umbilical cord sheath stump are of smaller diameter than the umbilical cord vessels in general, and contain straight and branched segments which are harvested and prepared for freeze-drying. The branched segments are in the form of a y-branch, which is the preferred graft alternative for some surgical applications.

At the time of graft utilization, preserved vessel 10 and canister 22 would be selected, based on the recipients needs with a patient under anesthesia. The patient's recipient site is exposed surgically. Under continuing sterile technique, canister 22 is opened by surgical attendants and the sterile unit 20 containing the freeze-dried preserve vessel 10 is removed. The vessel 10 and gauze carrier 18 are irrigated with saline solution for five minutes. The vessel is then removed from the stent 14 and the gauze carrier 18 for use and irrigated with heparin solution (300 U/ml) using smooth cannulation. Vessel 10 is sutured at each end, as it is implanted in the patient's recipient site, utilizing standard vascular anastomosis technique. Following release of vessel clamps of the recipients vessel, the surgeon would observe the flow and patency of the vessel to assure integrity of the graft.

While in the foregoing, embodiments of the present invention have been set forth in considerable detail for the purposes of making a complete disclosure of the invention, it may be apparent to those of skill in the art that numerous changes may be made in such detail without departing from the spirit and principles of the invention.

The following Examples are illustrative of the invention sought for patenting, but should not be deemed to limit the invention in any manner.

EXAMPLE 1

Grafts consisting of polytetrafluoroethylene (PTFE) in the form of tubes having a 1.0 mm internal diameter were carried out in 18 Sprague-Dawley rats. Each graft was 1 centimeter in length. The grafts were placed in one femoral artery of each rat to supply a 3×3 centimeter skin flap of the rat abdomen. The skin flap served as a visual indicator of graft patency.

Each rat was anesthetized with intraperitoneal pentobarbital having a concentration of 50 mg/kg. Each rat was secured on an operating board to allow access to the abdomen and inguinal areas. The abdominal area of each rat was shaved and antiseptic technique was used. A 3×3 cm abdominal skin flap (epigastric island flap) was incised and hemostasis was obtained. The femoral artery and vein, and their branches, as well as, the epigastric artery and vein for each rat, where identified. The epigastric vessels sup blood to the skin flap. The venous system was left intact. The femoral artery, proximal to the epigastric branch, was clamped with two vascular clamps, with excision of a 5-mm arterial segment. The arterial ends were irrigated with heparin solution (300 U/ml). Although the internal diameters of both the PTFE graft and the femoral artery where one centimeter, the significantly thicker walls of the PTFE graft required placing a continuous suture in a manner that would leave the end of the femoral artery within the lumen of the PTFE graft. A telescoping suture technique was used. The distal portion of the PTFE graft was then anastomosed to the distal portion of the femoral artery in a similar manner. The clamps were then released and the blood flow through the graft and into the epigastric pedicle was observed. The graft and abdominal skin where observed for five minutes. The "flicker test" was used to demonstrate flow in the superficial epigastric artery by gently elevating forceps on the undersurface of the artery and demonstrating pulsatile blood flow to that artery. Such blood was supplied through the emplaced PTFE graft. The skin was then sutured.

Two rats served as controls, in which the epigastric island flap was isolated and the epigastric artery was ligated, without placement of the PTFE graft. The flaps of the control animal demonstrated necrosis within 24 hours. The 18 rats with PTFE grafts demonstrated 50% patency. Sections of the grafts were taken for histologic and electron microscopy studies. Electron microscopy endothelial growth into the lumen of the PTFE graft from each end was noted. In essence, the telescoping suture technique accomplished the goal of anastomosing the dissimilar vessel ends, but the anastomosis technique was difficult to accomplish. Undesirably, the PTFE grafts remained rigid and served as rigid conduits. A PTFE graft of a longer length was seen to kink, which would preclude utilization of longer lengths of the graft, i.e., around a joint. However, this study indicated that endothelial proliferation through the lumina of the graft from each end occurred. It was concluded that a better graft material was needed.

EXAMPLE 2

17 Sprague-Dawley rats were utilized to develop epigastric island flaps, based on the inferior epigastric vessels which branch from the femoral vessels detailed hereinafter. 18 femoral vein segments from other rats were harvested for freeze-drying. To accomplish this task, each rat was anesthetized with interperitoneal Nembutal (50 mg/kg). Each rat was placed supine on a rat board and the abdominal skin was shaved. Using antiseptic technique and with the abdomen prepped, the right and left femoral veins were identified and clamped. A ten millimeter length of vein from each side was removed. The rats were then euthanized according to accepted humane techniques. The removed femoral grafts were irrigated with heparinized saline (300 U/ml). A nylon stent was then placed through the lumen, enclosed in a moist gauze carrier, and placed in a 10-cc freeze-dry vial. In this container, the grafts were then freeze-dried on a Virtis bench top, three model freeze-drier, manufactured by the Virtis Company, Inc. of Gardiner, N.Y. Freeze-drying was carried out over 24 hours at 0.4 atmospheres of pressure and at a temperature of minus 70° F. through the process of sublimation. In this process, the water within the specimen passes from a frozen crystalline state into the vapor state without expansion which occurs by freezing from the liquid state. Thus, the disruption of the integrity of the cellular structure of the vessel was avoided. Each specimen was stored at room temperature in the freeze-dry vial or canister with the vacuum seal being maintained.

The 17 Sprague-Dawley albino male rats weighing between 350 and 500 grams were then utilized for the femoral vein study. Each rat was anesthetized with intraperitoneal Nembutal (30 mg/kg) placed on a rat board, and the abdomen and groin were shaved. Using antiseptic technique, a 3×3-cm abdominal skin flap based on the epigastric artery and vein (epigastric island flap) was dissected. The femoral artery and vein, and the epigastric vessels to each island flap, were identified. The venus system was left intact. Two vascular clamps were placed on one femoral artery. A 6-mm arterial segment was excised. The cut ends of the femoral artery were then irrigated with heparinized saline (300 U/ml). The freeze-dried vessel was then obtained from one of the freeze-dried canisters, rehydrated with saline for 30 minutes, and anastomosed at the proximal cut end of the femoral artery using eight 10-0 Ethilon sutures under magnification, with a Carl Zeiss OpMi-6SD microscope. The distal anastomosis was completed in a similar manner. The clamp was then removed and blood was seen to flow through the vein graft into the epigastric artery. Patency was demonstrated using the "flicker test" as well as by the milking (strip) test. The femoral artery distal to the epigastric artery was then ligated. This technique allowed blood to flow through the freeze-dried graft, which had been placed as the sole arterial blood supply to the abdominal flap. The abdominal skin flap was then closed with a running 4-0 Vicryl suture. The flaps were then observed to be pink.

After two months, allowing enough time for collateral circulation to develop into the flaps, the patency of the vessel was demonstrated by anesthetizing the rat, with careful dissection through a groin incision to demonstrate the freeze-dried vessel segment. By observation, flicker and strip tests patency was determined. The patency rate was calculated to be 66%. Histologic and electron microscopy studies were carried out, demonstrating the presence of minimal intimal hyperplasia where the endothelial cells enter the graft lumen at each end from the femoral artery. Endothelialization was demonstrated as a thin epithelial layer within the lumen. Also, neovascularization of media and adventitia, as well as proliferation of fibroblasts, adjunct to the rebuilding of the vessel wall, were demonstrated. There was no evidence of graft rejection. The vein graft was noted to propagate the pulse visually and flicker and strip tests were readily demonstrated. Thus, the freeze-dried vessels were seen to undergo remodeling in vivo by a normal reparative process without evidence of cellular immune response.

EXAMPLE 3

15 Sprague-Dawley albino male rats were utilized to demonstrate the use of freeze-dried femoral arterial allografts. The arterial grafts were obtained from eight additional rats, each of which were anesthetized with intraperitoneal Nembutal (50 mg/kg) and then placed on a rat board. The abdominal and groin skin were then shaved and prepped. Antiseptic technique was utilized. The femoral arteries were identified, isolated by blunt and sharp dissection and then clamped to permit excision of a 1.0-cm section of each femoral artery. The grafts were then irrigated with heparinized solution (300 U/ml). A nylon stent was then placed in the lumen of each artery and the graft and stent were placed in a moist gauze carrier. A 10-mm vial or canister was then used to contain the graft, stent and carrier unit. The graft unit was then freeze-dried over 24 hours according to the parameters described in Example 2. The graft specimens were then stored on a shelf at room temperature maintaining the vacuum in the canister. The animals used for the donor vessels were subsequently euthanized in accordance with humane standards.

The 15 study animals heretofore described, were then utilized and prepared. The Sprague-Dawley rats, each weighing between 430-570 grams, were given intraperitoneal Nembutal (50 mg/kg) and placed on a rat board. The abdominal and groin areas were then shaved and antiseptic technique was utilized. With respect to each rat, a 3×3-cm epigastric island skin flap was incised and elevated, based on the epigastric artery and vein branching from the femoral vessels. Cardiovascular clamps were then placed on the femoral artery, permitting excision of a 6-mm arterial segment. The cut ends of the femoral artery were then irrigated with heparinized saline (300 U/ml). A freeze-dried artery was then obtained from the shelf canister or vial for each rat specimen. The artery was rehydrated in saline for 30 minutes. Proximal anastomosis was then completed with eight 10-0 Ethilon sutures under magnification. The individual sutures were placed sequentially in a circumferential manner for the anastomosis. The distal anastomosis was similarly completed. The clamps were then removed and circulation of the graft was noted, including circulation into the epigastric artery using flicker and strip testing. The femoral artery distal to the inferior epigastric artery was then ligated.

The sole arterial supply to the graft was noted to be through the freeze-dried graft. After rechecking patency the abdominal wound was closed with 4-0 Vicryl sutures. The observation of the abdominal flap demonstrated the presence of viability, indicative of graft patency. Although there was one kennel death from unrelated causes during a two month period, grafts in the 14 remaining rats exhibited a visual patency rate of 93% (13 of 14 flaps remaining visibly viable). The rats were anesthetized with interperitoneal nembutal (50 mg/kg), placed on a rat board, and the groin was shaved. An incision was carried down to the level of the graft, with 13 grafts being viable. After demonstration with the flicker and strip tests, sections of the graft were then recovered for histologic and electron microscopy studies the grafts were noted to have developed endothelial lining, stemming from each end of the graft. The vessel walls demonstrated normal healing processes. There was no evidence of graft rejection. The arteries were found to be easier to handle, being thicker walled facilitating the anastomosis. There was no evidence of aneurysmal dilatation.

EXAMPLE 4

20 New Zealand white female rabbits weighing between 2.6 and 5.8 Kg were utilized to study freeze-dried arterial grafts. Grafts were initially obtained from five other rabbits in which two femoral and two brachial arteries were harvested from each rabbit. The harvesting began with intermuscular Ketamine (50 mg/kg) and Xylazine hydrochloride (20 mg/kg) as an animal tranquilizer. Each animal was then placed under general anesthesia and maintained by oxygen and halothane delivered by mask. Each rabbit was placed on a board and the groin was shaved. Using sterile technique. Femoral and brachial arteries were identified and harvested in 3.5 to 4.0-cm vessel lengths. The grafts were then irrigated with heparinized saline (300 U/ml). A nylon stent was placed in each graft lumen. The graft and stent were placed in a moist gauze carrier, and then positioned in a 15 ml vial. The specimens within the vile were then freeze-dried over 24 hours, according to the techniques described in Example 2.

Following freeze-drying, the samples were stored on a shelf at room temperature maintaining the vacuum seal in the canister. The studied rabbits were then anesthetized in the before mentioned manner, and placed on a board. One femoral artery was identified through a longitudinal groin incision. A 2.0-cm segment of the femoral artery was excised, leaving a 3.5-cm defect secondary to vessel retraction from elastic recoil. The cut ends of the arteries were then flushed with heparinized saline (300 U/ml). Six of the rabbits received a brachial artery each having an internal diameter of 2 mm. Ten rabbits received femoral artery grafts, each having a 2.3 mm internal diameter. The grafts were then anastomosed as interpositional grafts using 10.0 Ethilon sutures under magnification. Clamps were then removed and the patency of the grafts was demonstrated visually through flicker and strip tests. Four other rabbits were used as a control group in which a 3.5-cm segment of femoral artery was removed and replaced as an autograft. Due to retraction, the defect following removal of the 3.5-cm segment was 4.5-cm. With reanastomosis of the sections, greater tension on the suture line was noted. The microvascular clamp were removed and patency was noted. In each rabbit, the skin incision was closed with running 4.0 nylon sutures. The six rabbits receiving brachial grafts exhibited no patency. Of the ten rabbits receiving femoral grafts, five exhibited patency. The four control animals exhibited no patency. The results of histologic and electron microscopy studies indicated the patent femoral arteries possessed neo-endothelization stemming from each end of the graft. There was no evidence of lymphocytic infiltration in the wall of any graft. Fibroblastic and myoblastic infiltration of the cell wall was noted as a normal reparative process. There was no evidence of immune response. It is concluded that the rabbit model proved more difficult than the study of the rat models of Examples 2 and 3.

EXAMPLE 5

A human placenta and an attached umbilical cord was received five hours post delivery. This tissue was placed in a sterile container with an overlying moistened surgical towel. The human placenta was removed from the container, grossly rinsed with saline, and placed on a dissection board. The cut ends of the two arteries and veins within the umbilical cord were easily identified and cannulated. Each vessel was then thoroughly irrigated with heparinized saline (300 U/ml), to clear the vessels of blood and clots and to prevent additional clotting by blood platelet remnants. The umbilical cord was laid out on an operating board. 6-power loupe magnification was employed in this regard. A longitudinal incision was made over the entire length of the umbilical cord through the outer sheath. The sheath was isolated from the vessels by dissection, bluntly, through the Wharton's Jelly and, sharply, by the incision of the attaching fibrous bands which extended from the vessel bundled to the sheath. The edges of the sheath were superiorly pinned to the board using marker pens with one rounded plastic end. The tissue was irrigated with saline every two minutes. In a similar manner, the lower edge of the sheath was separated from the vessels by blunt and sharp dissection techniques and pinned to the operating board. The three vessels were easily identified as two arteries in a helical spiral around the thicker-walled vein. The superficial portions of each vessel were then separated by blunt and sharp dissection at the peak of each spiral. A gentle spreading technique was employed to penetrate tissue planes between the vessels while the transverse fibrous bands were cut intermittently. Each vessel was freed circumferentially and the vessel loop was passed beneath the same to facilitate gentle traction of the vessel. Each vessel loop consisted of a colored plastic strand, 1 mm in diameter. Progressive freeing of the vessels was accomplished with continuing intermittent irrigation to maintain an acceptable moisture level. The vessels were then separated from each other and from the sheath. The fibrous band and sheath of the umbilical cord were also isolated. All in all, two veins, one artery, one fibrous band, and the sheath were presented for freeze-drying. The vessels were again irrigated with heparin solution (300 U/ml). A nylon stent, about 1 mm, was positioned within the lumen, to facilitate handling and to maintain separation of opposite vessel walls. The stents minimized direct handling of the vessel and acted as a carrier for the vessel during the freeze-drying and rehydration phases. In addition, it was determined that the vessels may be incised transversely to provide specific required lengths. The stents also accommodated vessels of differing resting diameters and allowed the capability of tapering of one end of the vessel for anastomosis of dissimilar ends. In addition, the vessels may be incised transversely to provide specific required lengths.

The vessels, sheath, and band are placed in individual canisters and key coded for identification. Each vessel with its positioned stent is covered by a moist gauze carrier and placed in the freeze-dried canister for lyophilization. Lyophilization takes place according to the steps of Example 2. The vessels are then stored, following lyophilization and by maintaining the vacuum and sterility within the canister, on a shelf at room temperature for subsequent use. Rehydration of the vessels requires removal from the canisters, soaking in heparinized saline for 20 minutes and removal of the stents from the cotton gauze carrier. Implantation of the vessel takes place following removal of the stent, and trimming of the end of the vessel to the length needed for implantation using standard vascular anastomosis techniques.

EXAMPLE 6

A fresh human placenta and attached umbilical cord were received from a donor within five hours of child birth. The placenta and attached umbilical cord had been maintained in a sterile container with overlying moist surgical towel. After receipt, the placenta and cord were grossly rinsed with saline to remove external maternal matter and fetal blood and clots.

The cord and placenta were then placed on a sterile moist towel overlying a dissection board. The umbilical cord was incised transversely, approximately 1 centimeter from its insertion into the placenta, and was placed stored temporarily in a sterile container with overlying moist towel, pending further processing. The cord measured 10 inches long, however other cords were prior observed to have a length of up to 36 inches in some instances.

The placenta, which measured 8 inches in diameter, was rinsed with heparinized saline solution (300 U/ml). The stumps of the umbilical vein and the two umbilical arteries were then isolated, and, with smooth cannulation, were irrigated with heparinized saline (300 U/ml) to remove residual fetal blood remnants.

The placenta, with its thin overlying amniotic membrane, permitted easy visualization of the placental vessels with inter-twining of the arteries and veins. The placenta was visualized to determine whether these vessels have a dispersed pattern with immediate branching into multiple small vessels, or majestral pattern with branching into fewer larger vessels and, subsequently, into multiple smaller terminal branches.

The umbilical cord sheath was first incised longitudinally, and then along the dorsal aspect of the placenta. Smooth and sharp dissection was used to identify and isolate the larger veins and arteries. It was further realized that further dissection would be needed to concentrate on selected vessels, since there was a wide variety of vessel options to be processes, including branched, unbranched, larger or smaller vessels, which may be cut to varying vessel lengths.

In this case, the distal portions of the umbilical cord artery and vein, each with large trunk branching as they enter the superficial surface of the placenta, were isolated. Additional straight vessels, arteries and veins were then isolated. Vessels with branching were also isolated.

Each of these vessels were isolated initially by blunt dissection, with vessel loops placed underneath for gentle traction. The remainder of each vessel was then isolated by blunt and sharp dissection to free them from adjacent tissues by cutting connective tissue bands. Once each segment was freed, they were kept moist, by re-irrigating with heparinized saline (300 U/ml). During the dissection of the smaller vessels, unnecessary tributaries were tied off.

Nylon stents were then placed within the grafts. Two stents, ie: 1 mm diameter, are placed through the common base, with each stent exiting through a different terminal branch. The use of stents in this manner facilitated further handling of the graft and maintained separation of the opposing walls of the vessel. With additional irrigation of heparinized saline, the grafts experienced minimal trauma during handling, with the endothelial cells lining the lumen being essentially undisturbed. There was no effort to expand, compress, or taper the vessels. Each vessel and stent was then placed in a moist cotton carrier, which was then positioned within a freeze-dry canister. The canister remained refrigerated until the freeze-drying process was initiated. The freeze-drying was carried out by a standard freeze-drying method utilizing a Virtis freeze-drying processor. Following freeze-drying, the vessel, which contains no moisture, was maintained in a vacuum state within the canister, resting in the gauze carrier. The canister was then stored, at room temperature. It is believed the potential storage life may extend for years, using this technique.

At the time of utilization as a replacement vessel the selected freeze-dried vessel was prepared by opening the canister to restore atmospheric temperature, and in a sterile manner, the gauze carrier was extracted from the canister, and placed on the sterile operating field. The vessel and cotton carrier were then irrigated with heparinized saline (300 U/ml) for approximately five minutes. At this point the vessel with the enclosed stents was removed from the cotton carrier. At the place of utilization on the surgical field, the stents were removed, and the vessel was then anastomosed into place using standard microsurgical technique under loupe or operating microscope magnification.

In addition to the heretofore described utilization as a replacement vessel it is believed the rehydrated vessel may be used as a neural tube carrier to potentiate the regeneration of peripheral nerves. Additional uses may consist of replacement of tubular structure in the body including, but not limited to, the ureter, urethra, fallopian tube and the gall bladder duct.

The following claims are herein provided to describe the present invention.

The invention claimed is:

1. A vascular graft suitable for implantation in an adult human, comprising:
   a preserved, isolated vessel isolated from a human umbilical cord or human placenta, wherein the isolated vessel is directly lyophilized without chemical denaturing said preserved vessel being substantially free of fetal blood; and
   a removable stent to facilitate handling of the preserved vessel, wherein the removable stent is located in a lumen of said preserved, isolated vessel prior to implantation;
   wherein following rehydration of the preserved, isolated vessel is suitable for implantation in an adult human.

2. The vascular graft of claim 1, in which said preserved, isolated vessel is a vein.

3. The vascular graft of claim 1 in which said preserved, isolated vessel is an artery.

4. The vascular graft of claim 1 in which said preserved, isolated vessel is free of fetal blood by way of irrigation.

5. The vascular graft of claim 1 in which said preserved, isolated vessel comprises a straight vessel segment.

6. The vascular graft of claim 1 in which said preserved, isolated vessel comprises a branching vessel segment.

7. The vascular graft of claim 4 in which said preserved, isolated vessel free of fetal blood by irrigation is free of fetal blood through irrigation with heparin solution.

8. The vascular graft of claim 1 in which said stent is a nylon stent.

9. The vascular graft of claim 1 in which said preserved, isolated vessel possesses a plurality of branches and further includes a plurality of removable stents each located in a lumen of each of said plurality of branches of said preserved, isolated vessel prior to implantation, wherein the removable stents facilitate handling of the preserved, isolated vessel.

10. The vascular graft of claim 9 in which said plurality of stents comprise nylon stents.

11. A preserved, isolated vessel suitable for implantation as a vascular graft in an adult human produced by direct lyophilization without chemical denaturing of an isolated vessel isolated from a human umbilical cord or human placenta, wherein said preserved, isolated vessel comprises a removable stent located in a lumen of said preserved, isolated vessel to facilitate handling of the preserved, isolated vessel;
wherein following rehydration of the preserved, isolated vessel is suitable for implantation in an adult human.

12. The preserved, isolated vessel of claim 11 in which said preserved, isolated vessel is a vein.

13. The preserved, isolated vessel of claim 11 in which said preserved, isolated vessel comprises a straight vessel segment or a branching vessel segment.

14. The preserved, isolated vessel of claim 11 in which fetal blood is removed from the vessel by irrigation.

15. The preserved, isolated vessel of claim 14 in which irrigation is performed with a heparin solution.

16. The preserved, isolated vessel of claim 11 in which said stent is a nylon stent.

17. The preserved, isolated vessel of claim 11 in which said preserved vessel possesses a plurality of branches and further includes a plurality of removable stents each located in a lumen of each of said plurality of branches of said preserved, isolated vessel prior to implantation, wherein the removable stents facilitate handling of the preserved vessel.

18. The preserved, isolated vessel of claim 17 in which said plurality of removable stents comprise nylon stents.

19. A method for implanting a vascular graft, the method comprising:
rehydrating the preserved, isolated vessel of claim 11; and
implanting the rehydrated vessel into a recipient site in a human patient.

20. The method of claim 19, wherein the method further comprises removing said removable stent prior to completing said implanting.

21. A vascular graft suitable for implantation in an adult human, consisting essentially of:
a preserved, isolated vessel isolated from a human umbilical cord or human placenta, wherein the vessel is lyophilized without chemical denaturing; and
a removable stent positioned in a lumen of the preserved vessel prior to implantation to facilitate handling of the preserved, isolated vessel;
wherein following rehydration of the preserved, isolated vessel is suitable for implantation in an adult human.

22. A containerized preserved, isolated vessel comprising:
a canister; and
a preserved, isolated vessel according to claim 1 contained in the canister,
wherein the canister is capable of maintaining the preserved, isolated vessel in a sterile environment.

23. The containerized preserved vessel of claim 22, wherein the canister comprises a vacuum seal to maintain storage of the preserved, isolated vessel under vacuum.

24. A containerized preserved, isolated vessel consisting essentially of:
a canister; and
a preserved, isolated vessel according to claim 1 contained in the canister
wherein the canister is capable of maintaining the preserved vessel in a sterile environment.

25. The containerized preserved, isolated vessel of claim 24, wherein the canister comprises a vacuum seal to maintain storage of the preserved, isolated vessel under vacuum.

26. The preserved, isolated vessel of claim 11 in which said preserved, isolated vessel is an artery.

27. The vascular graft of claim 1, wherein the preserved, isolated vessel is produced from a vessel isolated from a human umbilical cord.

28. The vascular graft of claim 1, wherein the preserved, isolated vessel is produced from a vessel isolated from a human placenta.

29. The preserved, isolated vessel of claim 11, wherein the preserved, isolated vessel is produced from a vessel isolated from a human umbilical cord.

30. The preserved, isolated vessel of claim 11, wherein the preserved, isolated vessel is produced from a vessel isolated from a human placenta.

31. The vascular graft of claim 21, wherein the preserved, isolated vessel is produced from a vessel isolated from a human umbilical cord.

32. The vascular graft of claim 21, wherein the preserved, isolated vessel is produced from a vessel isolated from a human placenta.

33. The containerized preserved, isolated vessel of claim 22, wherein the preserved, isolated vessel is produced from a vessel isolated from a human umbilical cord.

34. The containerized preserved, isolated vessel of claim 22, wherein the preserved, isolated vessel is produced from a vessel isolated from a human placenta.

35. The containerized preserved, isolated vessel of claim 24, wherein the preserved vessel is produced from a vessel isolated from a human umbilical cord.

36. The containerized preserved, isolated vessel of claim 24, wherein the preserved, isolated vessel is produced from a vessel isolated from a human placenta.

37. A method for implanting a graft in an adult human, the method comprising:
rehydrating a preserved, isolated vessel produced by direct lyophilization without chemical denaturing of an isolated vessel isolated from a human umbilical cord or human placenta, wherein said preserved, isolated vessel comprises a removable stent located in a lumen of said preserved, isolated vessel to facilitate handling of the preserved, isolated vessel, and wherein following rehydration the preserved, isolated vessel is suitable for implantation in an adult human;
removing the removable stent; and
implanting the rehydrated vessel into a recipient site in an adult human patient.

38. The method of claim 37, wherein the removable stent is removed prior to said implanting.

39. The method of claim 37, wherein the preserved, isolated vessel is produced by direct lyophilization without chemical denaturing of a vessel isolated from a human umbilical cord.

40. The method of claim 37, wherein the preserved, isolated vessel is produced by direct lyophilization without chemical denaturing of a vessel isolated from a human placenta.

* * * * *